United States Patent
Minnigh et al.

(10) Patent No.: US 7,531,822 B1
(45) Date of Patent: May 12, 2009

(54) MANAGEMENT OF ERASURE INTERVALS FOR STORAGE MEDIUM OF A RADIOGRAPHY CASSETTE

(75) Inventors: Todd R. Minnigh, Pittsford, NY (US); Xiaohui Wang, Pittsford, NY (US)

(73) Assignee: Carestream Health, Inc., Rochester, NY (US)

( * ) Notice: Subject to any disclaimer, the term of this patent is extended or adjusted under 35 U.S.C. 154(b) by 0 days.

(21) Appl. No.: 11/926,242

(22) Filed: Oct. 29, 2007

(51) Int. Cl.
*G01N 23/04* (2006.01)

(52) U.S. Cl. .................. 250/588; 250/580; 250/581; 250/582

(58) Field of Classification Search .............. None
See application file for complete search history.

(56) References Cited

U.S. PATENT DOCUMENTS

| | | | | |
|---|---|---|---|---|
| 4,584,483 A | * | 4/1986 | Kato | 250/459.1 |
| 4,760,256 A | * | 7/1988 | Ohgoda et al. | 250/588 |
| 6,379,044 B1 | * | 4/2002 | Vastenaeken et al. | 378/207 |
| 2004/0005033 A1 | * | 1/2004 | Nishihara et al. | 378/169 |
| 2007/0018125 A1 | * | 1/2007 | Fletcher-Heath et al. | 250/581 |

* cited by examiner

*Primary Examiner*—David P Porta
*Assistant Examiner*—Yara B Green

(57) ABSTRACT

An apparatus for obtaining a radiographic image has a cassette with an erasable photostimulable storage medium, housed in the cassette, that can store a radiographic image when irradiated with electromagnetic radiation at an exposure wavelength and that can be erased for subsequent use when irradiated with electromagnetic radiation at an erasure wavelength. A memory that is associated with the cassette stores a signal that is indicative of elapsed time since the most recent erasure of the photostimulable medium.

14 Claims, 6 Drawing Sheets

MANAGEMENT OF ERASURE INTERVALS FOR STORAGE MEDIUM OF A RADIOGRAPHY CASSETTE

FIELD OF THE INVENTION

This invention generally relates to computed radiography and more particularly relates to the management of erasure intervals for improving the performance of storage mediums of computed radiography cassettes.

BACKGROUND OF THE INVENTION

In a storage phosphor computed radiography (CR) system, a photostimulable storage medium, such as a sheet or plate of storage phosphor, also known as a stimulable phosphor, is exposed to x-ray radiation that has been directed through an object or organ, such as a body part of a patient, to record a latent radiographic image in the storage phosphor. The latent radiographic image stored from the x-ray exam is then read out by stimulating the storage phosphor with stimulating radiation of a read wavelength, such as red or infra-red radiation, produced by a laser or other intense light source. Upon stimulation at the read wavelength, the storage phosphor emits stimulated radiation of an emission wavelength, such as blue radiation. In a CR system, the storage phosphor is typically scanned by a laser beam which provides the read wavelength and the stimulated radiographic image at the emission wavelength is detected by a photodetector to produce an electronic radiographic image. The image can then be digitized and stored, transmitted, or output on a display or recorded onto a radiographic film.

After it is read, the storage phosphor sheet, herein termed the CR plate or storage medium, is then erased so that it can be reused. Erasure of the stimulable phosphor material is typically performed using a high-intensity lamp that emits visible light having suitable spectral characteristics. Erasure uses a different range of wavelengths than those used for recording or reading the radiographic image. For example, high-brightness fluorescent light is often used for erasure. The newly erased CR plate is then stored back in its cassette, ready for re-use.

One problem with the CR plate relates to the sensitivity of the stimulable phosphors used on the CR plate. Even in a protected environment, the stimulable phosphors themselves, following erasure, are still sensitive to environmental radiation including cosmic rays, X-rays emitted from nearby X-ray sources, and trace radiation sources, including those on the CR plate itself and from its surroundings. Understandably, it would be a formidable task to formulate the stimulable phosphors so that they are less sensitive to such environmental radiation without compromising imaging performance at the same time. The problem of sensitivity to environmental radiation has other repercussions, including added noise content for diagnostic images. This, in turn, tends to increase the relative dose levels needed for diagnostic imaging in order to maintain acceptable signal-to-noise (SN) levels.

This sensitivity to environmental radiation limits the useful storage time or "shelf life" of the CR cassette following erasure. If the time interval since its last erasure is too long, imaging may not be satisfactory. Recognizing this problem, some CR imaging technologists or radiographers attempt to recycle and re-use CR cassettes in a sequential order according to relative erasure time. Using a cassette management sequence of this type, the CR cassette having the longest time since its last erasure is used first, with others sequenced in order of their relative time since last erasure. While manual record-keeping and cassette recycling practices have merit, however, they are prone to error.

SUMMARY OF THE INVENTION

It is an object of the present invention to address the need for improved management of erasure intervals for storage mediums of CR cassettes. With this object in mind, the present invention provides an apparatus for obtaining a radiographic image comprising:
 a) a cassette;
 b) an erasable photostimulable storage medium, housed in the cassette, that can store a radiographic image when irradiated with electromagnetic radiation at an exposure wavelength and that can be erased for subsequent use when irradiated with electromagnetic radiation at an erasure wavelength; and
 c) a memory that is associated with the cassette and that stores a signal that is indicative of elapsed time since the most recent erasure of the photostimulable medium.

From another aspect, the invention provides a method for obtaining a radiographic image comprising:
 a) erasing a photostimulable medium that is housed in a cassette;
 b) recording a time of erasure associated with the cassette by setting a memory signal to a predetermined value; and
 c) providing an indication of time elapsed since erasure according to the memory signal.

It is a feature of the present invention that it stores information that can be used by radiology personnel to determine the relative time interval since last erasure for a CR cassette.

It is an advantage of the present invention that it provides tools that help to automate the management or erasure intervals for storage mediums for CR cassettes.

The invention and its objects and advantages will become more apparent in the detailed description of the preferred embodiment that follows.

BRIEF DESCRIPTION OF THE DRAWINGS

While the specification concludes with claims particularly pointing out and distinctly claiming the subject matter of the present invention, it is believed that the invention will be better understood from the following description when taken in conjunction with the accompanying drawings, wherein:

DETAILED DESCRIPTION OF THE INVENTION

It is to be understood that elements not specifically shown or described may take various forms well known to those skilled in the art.

Figure 1:
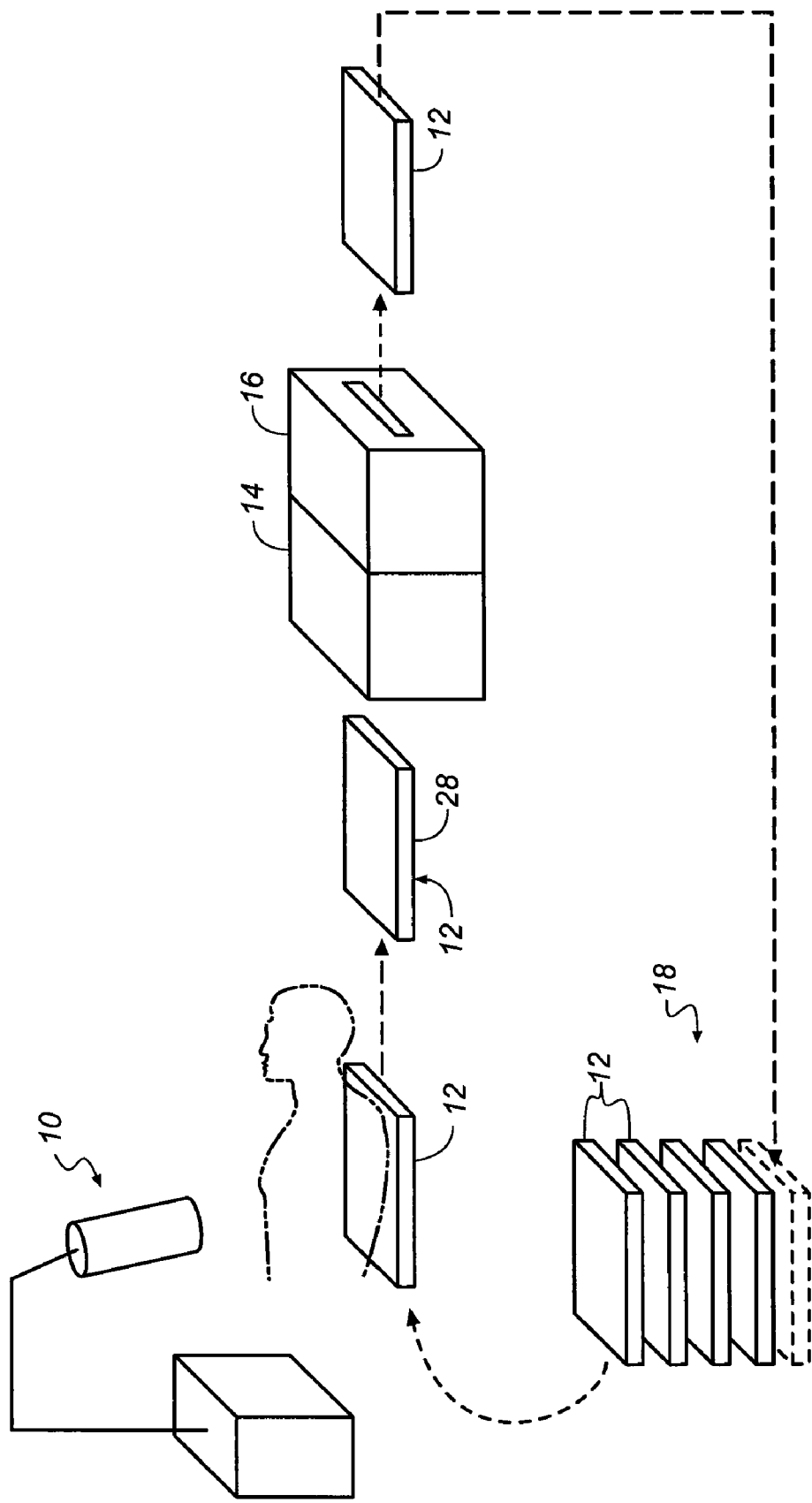
FIG. 1 is a schematic illustration of a representative system for cycling CR cassettes for use in a first-in first-out manner.

The apparatus and method of the present invention provide a system for cycling CR cassettes using first-in, first-out CR cassette management. Referring to FIG. 1, there is shown a schematic illustration of a representative system for cycling CR cassettes for use in a first-in first-out manner. An x-ray apparatus 10 forms a latent image on a sheet or plate of erasable photostimulable storage medium (shown in FIG. 6) that is typically, though not necessarily, is removably housed within a cassette housing 28 of a CR cassette 12. Cassette 12 is then input to a reader 14 that obtains the latent image by irradiating the storage medium with a read wavelength. The latent image is then read out by conventional devices, not shown. Coupled with reader 14 in most systems is an erasure section 16 that removes any residual latent image from the stimulable phosphor plate by irradiating at an erasure wavelength once the plate has been read, thereby readying cassette 12 for re-use. Once the medium within cassette 12 has been erased, the cassette is moved to a storage area 18, shown simply as a stack of cassettes 12. In a well-managed system, each x-ray exam uses the cassette 12 having the longest time period since its last erasure.

As was noted earlier in the background section, however, manually maintaining an orderly re-use cycling arrangement for cassette 12 in storage area 18 is error prone. Moreover, even where an orderly system has been enforced, the radiology technician has no knowledge of how long a particular cassette 12 has been in storage since its last erasure. In any case, unless the information is accurately recorded in some way, the technician has no way of knowing the erasure times for any particular cassette 12.

Figure 2:
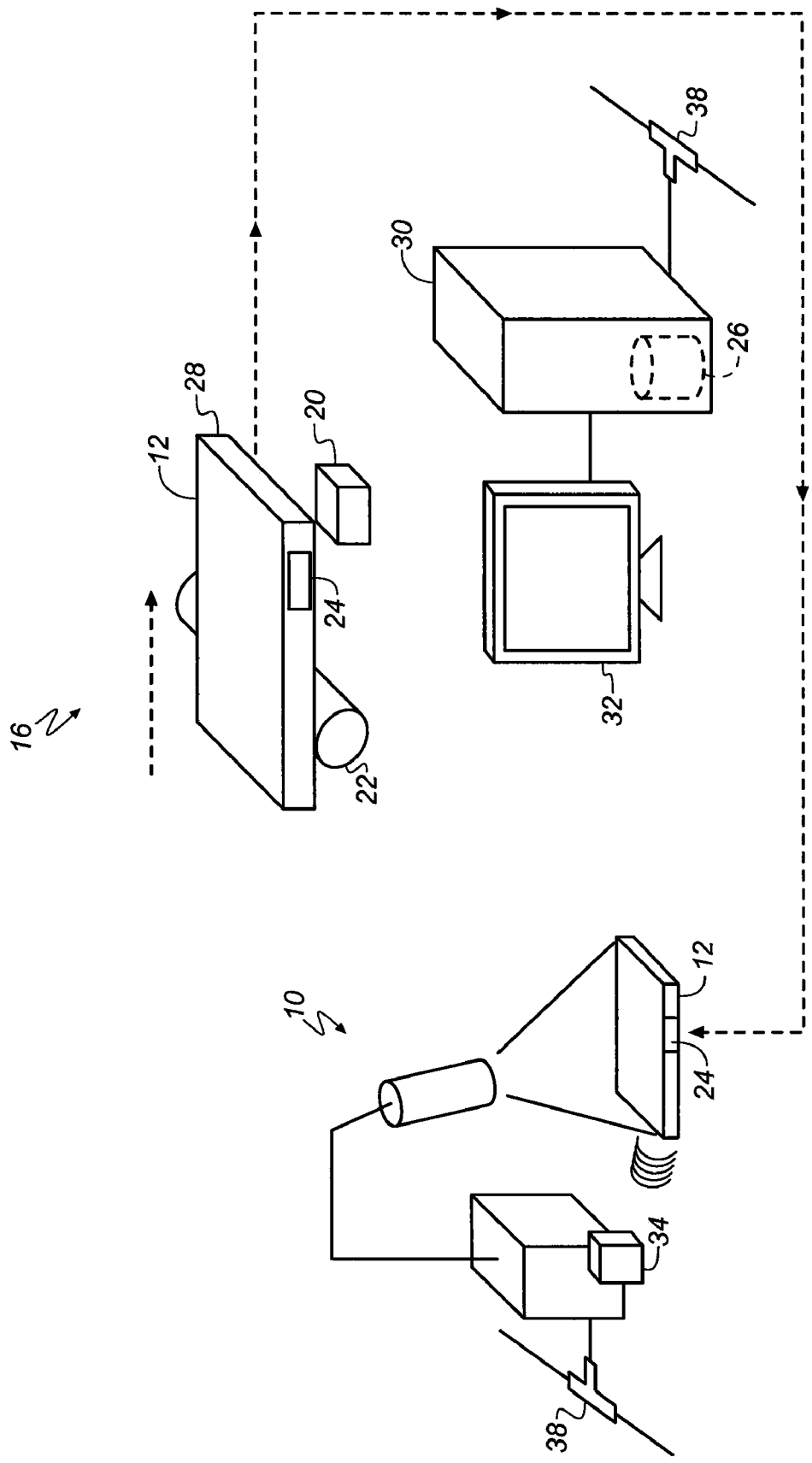
FIG. 2 is a schematic illustration of an embodiment for sensing or recording erasure and sensing the interval since last erasure at the x-ray apparatus.
Figure 4:
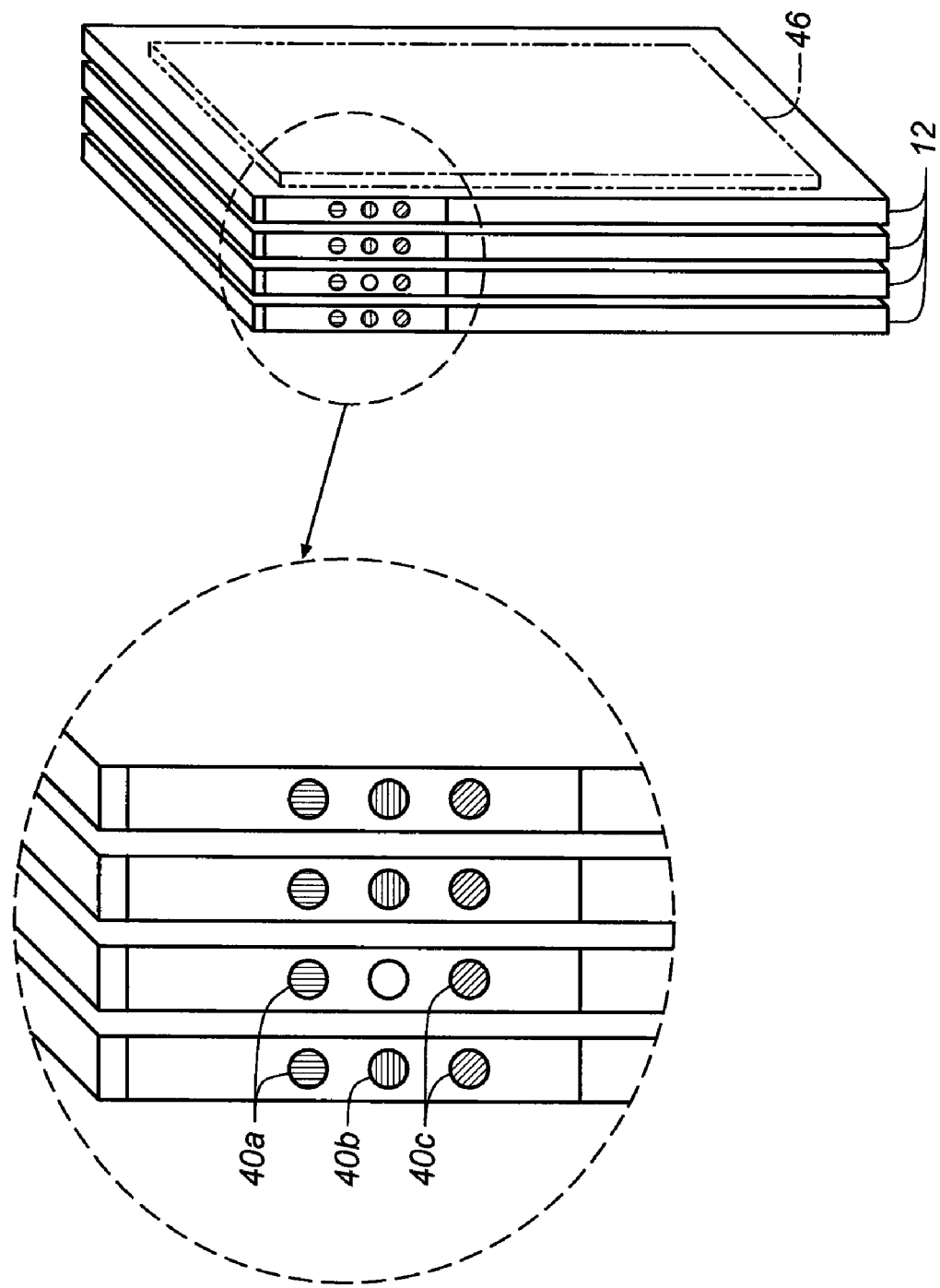
FIG. 4 is a perspective diagram showing indicators of erasure interval as provided on one side of the CR cassette in one embodiment.

The schematic illustration of FIG. 2 shows a system for managing cassettes 12 at an imaging site according to one embodiment of the present invention. Within erasure section 16, energy for erasure at the erasure wavelength is applied to cassette 12, typically from an erasure light 22 or other radiant source. As part of the erasure cycle in this embodiment, a sensor 20 detects an identifier 24 that is coupled to cassette 12. Identifier 24 stores an identifying number, name, or code that distinguishes each cassette 12 from others at the site. This data is stored as a signal in a memory 26, which can reside on cassette 12 itself, as discussed with regard to FIGS. 4 and 5, or can be stored on a separate external host processor 30 as shown in FIG. 2. Sensor 20 senses identifier 24 and reports the time of erasure to host processor 30, recording this time in memory 26. Sensing can use light, such as using a bar-code or other visually encoded device, or can use some other means for obtaining identifier 24 data. In one embodiment, identifier 24 includes RF transponder components so that sensor 20 communicates as a type of transceiver using wireless RF signals. Magnetically encoded components could alternately be used.

Cassette 12 is then ready for re-use, and the time since its last erasure is recorded using memory 26. This information in memory 26 can be made accessible on a display 32, for example, or can be stored or provided electronically, as well as being available from a printout, label, tag, sticker or other mechanism.

X-ray apparatus 10 has a coupled sensor 34 that detects identifier 24 on each CR cassette 12 prior to exposure. As shown in FIG. 2, detection may be wireless, such as using RFID or similar devices for communication between sensor 34 and identifier 24. Non-contact sensing, such as barcode identification could be employed. Alternately, some type of contact sensing could be used. A network connection 38 enables x-ray apparatus 10 to obtain information from host processor 30, including stored date and time of last erasure for the cassette 12 that is ready for imaging. This information could be displayed for the technician on display 32.

Depending on requirements established for one or more sites, the time period since last erasure could be a factor controlling operation of x-ray apparatus 10 with any particular cassette 12. A warning could be issued if an excessive amount of time has elapsed since a particular cassette 12 has been erased. In an extreme case, where the time period since last erasure for a particular cassette 12 exceeds a threshold value, x-ray apparatus 10 may be disabled from exposure operation when using that cassette 12.

Figure 3:
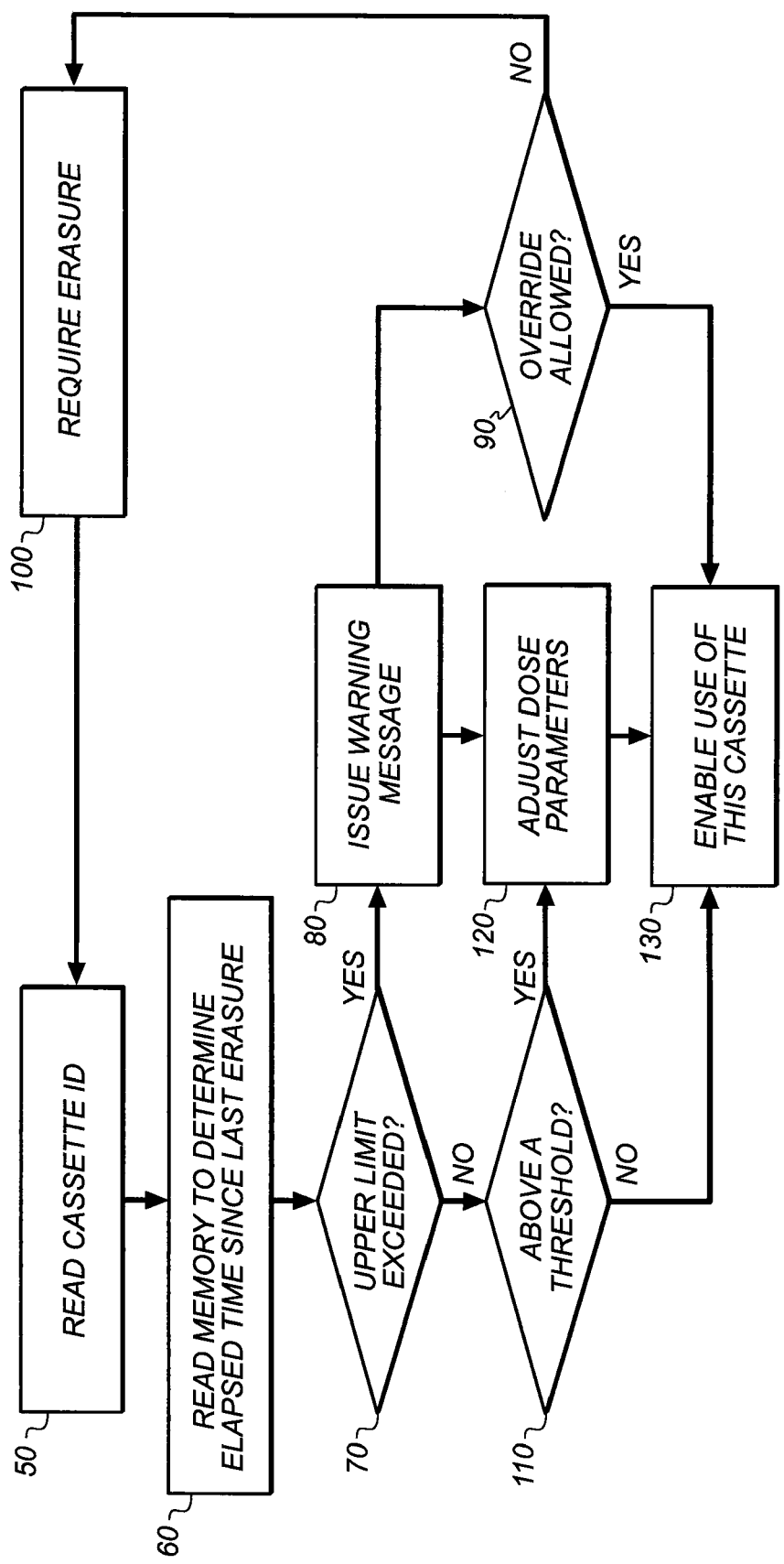
FIG. 3 is a logic flow diagram showing steps for system monitoring and response to recorded time since erasure in one embodiment.

Referring to FIG. 3, there is shown a logic flow diagram of steps used for system monitoring and response to recorded time since erasure in one embodiment. This process begins with an identification step 50 in which the specific cassette that is intended for imaging is identified. This identification may use a bar code or other encoded information that can be obtained using hard-wired or wireless sensing methods, as described earlier with reference to FIG. 2. From this identification, the memory 26 is referenced, so that an elapsed time determination step 60 is executed. As part of this step, information that discloses the time interval since the last erasure is obtained from memory 26 (FIG. 2). This memory data may be obtained from data that is stored on cassette 12 itself or from information stored in a database that is in communication with erasure apparatus, for example. A limits decision step 70 is next executed, which tests to determine if the interval since last erasure is acceptable for imaging and checks whether cassette 12 requires erasure before imaging can continue. A warning step 80 follows if this time duration is excessive. An override decision step 90 may then be provided, allowing the operator to override the erasure requirement, such as in an emergency, for example. If override is not allowed, an erasure requirement step 100 is performed, instructing the operator to erase the cassette or use another, and control then returns to identification step 50. If, on the other hand, override is permitted, imaging that uses this cassette can proceed, and control passes to an enablement step 130.

Where the interval since last erasure is acceptable, a threshold decision step 110 executes. Here, for a cassette that is still considered to be usable, it may be desirable to adjust exposure parameters to compensate for higher noise levels. A dose parameters adjustment step 120 is executed when the elapsed time is higher than a predetermined threshold. In dose parameters adjustment step 120, technique variables such as kVp setting, AEC value, or mAs value can be adjusted by the operator to increase exposure in this way. Finally, enablement step 130 allows the use of the particular cassette 12 for imaging.

It can be appreciated that the logic shown in FIG. 3 is by way of example, not of limitation, and admits a number of variations for managing erasure intervals for cassette 12. For example, override (step 90) may not be allowed in cases where the interval since last erasure is excessive, effectively preventing use of cassette 12 until its time since last erasure is within acceptable range. More than one threshold could be tested, so that there are effectively multiple threshold decision steps 110, with variable parameter adjustment in step 120 based on which threshold is exceeded. It may not be acceptable to disable use of any particular cassette, in enablement step 130. Instead, warning messages could be posted to the operator or could be saved with the image metadata.

Referring back to FIG. 2, it can be appreciated that using and tracking identifier 24 can provide a useful way for maintaining information in memory on the time period since its last erasure for each cassette 12 at a site. Moreover, additional steps can be taken to make this information readily available and visible to radiology personnel. Referring to the perspective view of FIG. 4, there is shown an example using indicators 40a, 40b, and 40c, of different colors and located at different positions on cassettes 12. In one embodiment, only one of indicators 40a, 40b, or 40c is ON at a time, based on the elapsed time since last erasure. Alternately, one or more of these indicators may also manifest the status of the cassette using a blinking or flashing pattern, such as to indicate when erasure is overdue. A photostimulable medium 46 that is internal to cassette 12 is shown in phantom for one of the cassettes 12 in FIG. 4.

Figure 5:
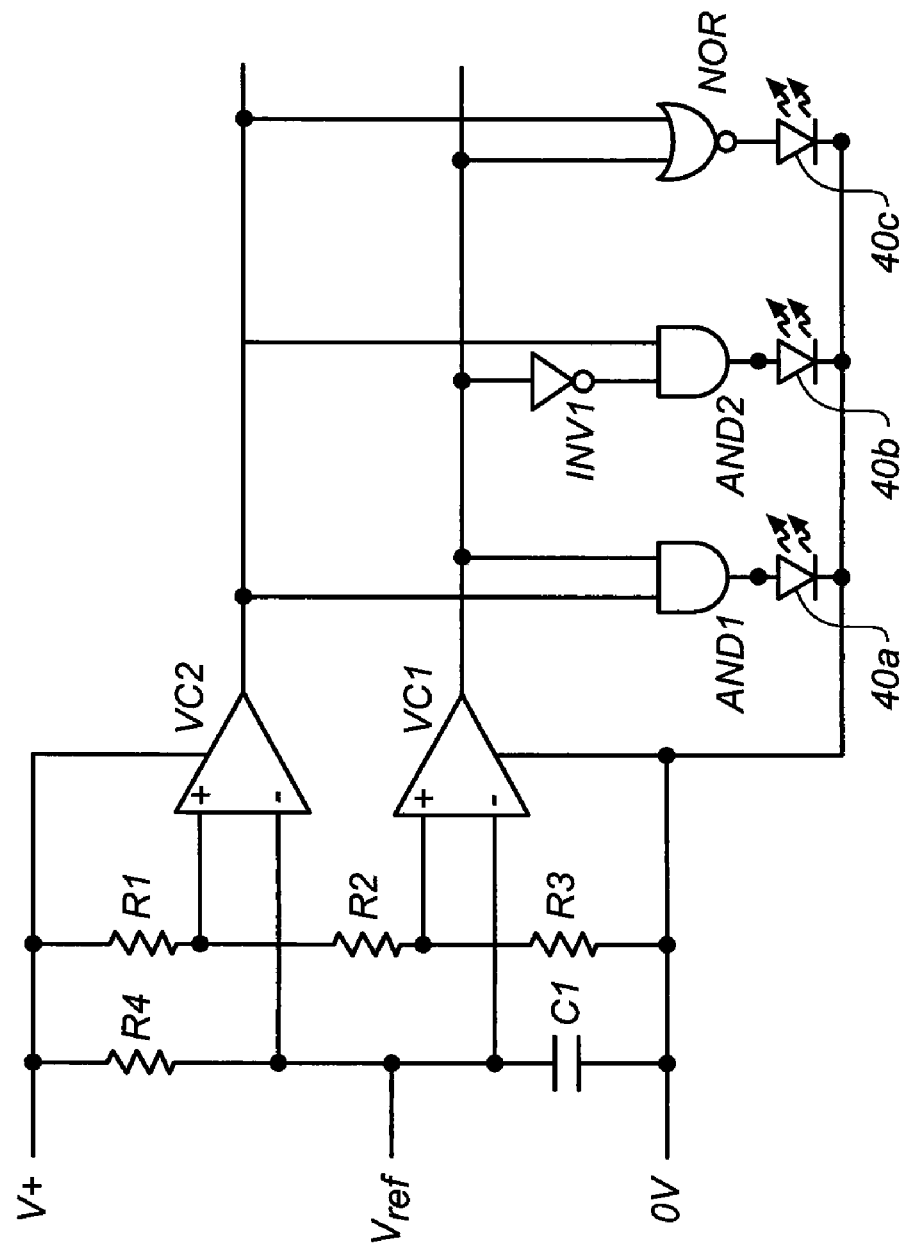
FIG. 5 is a schematic diagram of a circuit for providing an erasure timing indicator.

Memory 26 can record a signal that is in the form of a digital data value or can store a timer value, for example. The schematic diagram of FIG. 5 shows how an analog memory 26 using a timer circuit works for storing a memory signal in one embodiment suitable to be mounted on cassette 12. Here, indicators 40a, 40b, and 40c can be actuated or energized in sequence, based on a time constant. A charging capacitor C1 provides a mechanism for storing an analog charge that serves as a memory signal indicating the time since the preceding erasure. Charging capacitor C1 is discharged at the time of erasure using known electrical or electro-mechanical techniques, which basically clears the memory as a form of initialization. Following erasure, applied voltage V+ then begins to charge capacitor C1 through resistor R4 and voltage $V_{ref}$ begins to increase accordingly. Resistor R4 and capacitor C1 thus provide an RC time constant for the reference voltage $V_{ref}$ at inverting inputs of comparators VC1 and VC2. Initially, there is very little charge across capacitor C1, resulting in a minimal reference voltage $V_{ref}$ at the inverting input of voltage comparators VC1 and VC2. Series resistors R1, R2, and R3 form a voltage divider, providing reference voltages from the voltage source V+. Initially, AND-gate AND1 that drives indicator 40a is high, providing current to indicator 40a. The second AND-gate, AND2, that drives indicator 40b is low, as is the NOR-gate that drives indicator 40c. As reference voltage $V_{ref}$ rises above the first voltage divider level over time, indicator 40a is switched OFF and indicator 40b is switched ON due to the action of inverter INV1 at AND-gate AND2. As reference voltage $V_{ref}$ then rises above the second threshold voltage level after another time period, indicator 40b goes OFF and indicator 40c is energized. Sensor 34 then can check the status of indicators 40a-40c to detect a measure of erasure interval.

It can be readily appreciated by those skilled in the electronic arts that the basic embodiment described with reference to FIG. 5 provides one useful way to indicate elapsed time, effectively using an analog timer as memory 26. This basic arrangement admits any of a number of modifications, including the use of potentiometers for one or more of resistors R1-R4 and other configurations of logic gates for driving indicators 40a-40c as well as fewer or additional indicators along with their corresponding voltage sensing and drive circuitry.

Figure 6:
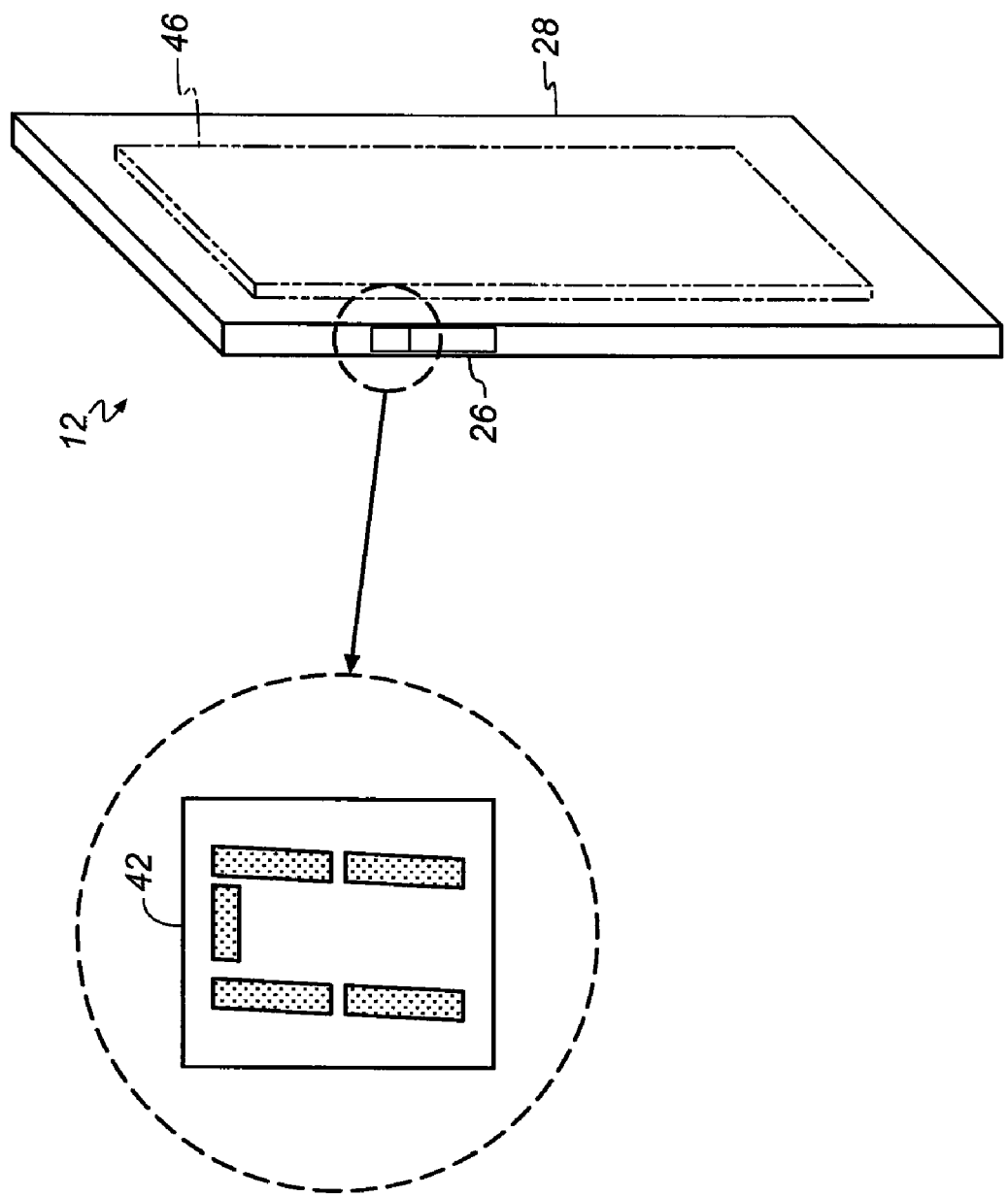
FIG. 6 is a perspective diagram showing a timer display showing time since last erasure in an alternate embodiment.

FIG. 6 shows another embodiment in which a timer or other suitable indicator 42 is displayed on cassette 12 itself. In the embodiment shown in FIG. 6, indicator 42 is a liquid crystal (LC) display showing numeric digits that indicate elapsed time since the last exposure that was obtained for cassette 12. It can be appreciated that any of a number of other types of indicators could similarly be used.

The present invention provides a memory that is associated or coupled in some way with cassette 12, whether the memory resides on cassette 12 itself by being built into or attached onto cassette 12, or is stored at some other location. The type of memory that is used and, correspondingly, the type of signal that is stored as a predetermined initialization value, can vary widely between applications. Where cassette 12 has a unique identifier, such as a barcode or other encoding that differentiates one cassette from another, a time stamp can be associated with the encoding and this predetermined data signal stored on cassette 12 or on an external host computer or other host processor that tracks erasure timing and is updated when the cassette 12 contents are erased. Built-in circuitry and indicators could be provided as analog memory for cassette 12, such as those described with reference to FIGS. 4 and 5. A digital timer could be built into or added onto cassette 12 for providing this memory function, storing or displaying a digital signal as was described with reference to FIG. 6. In an alternate embodiment, wireless transmission could be used to provide information on elapsed time from cassette 12 to a host processor.

The invention has been described in detail with particular reference to certain preferred embodiments thereof, but it will be understood that variations and modifications can be effected within the scope of the invention as described above, and as noted in the appended claims, by a person of ordinary skill in the art without departing from the scope of the invention. For example, memory 26 can be stored either on cassette 12 itself or can be stored at an external host such as host processor 30 in FIG. 2. Memory 26 can be embodied in a number of different ways, using either or both analog and digital signals. Charging capacitor C1 as was described with reference to FIG. 5 is but one example of an analog memory device. Other types of devices could indicate elapsed time using other analog techniques such as devices that change color over time due to oxidation or other chemical changes. Memory 26 could be activated or reset by mechanical actuation, such as during handling of the CR plate for erasure, or as a result of receiving erasure wavelengths.

Thus, what is provided is an apparatus and method for the management of erasure intervals for improving the performance of computed radiography cassettes.

PARTS LIST

10 X-ray apparatus
12 Cassette
14 Reader
16 Erasure section
18 Storage area
20 Sensor
22 Erasure light
24 Identifier
26 Memory
28 Cassette housing
30 Host processor
32 Display
34 Sensor
38 Network connection
40a, 40b, 40c. Indicator
42 Indicator
46 Photostimulable medium
50 Identification step
60 Elapsed time determination step
70 Limits decision step
80 Warning step
90 Override decision step
100 Erasure requirement step
110 Threshold decision step
120 Dose parameters adjustment step
130 Enablement step
C1 Capacitor
R1, R2, R3, R4 Resistor
VC1, VC2 Voltage comparator
V+ Voltage source

The invention claimed is:

1. An apparatus for obtaining a radiographic image comprising:
   an erasable photostimulable storage medium that can store a radiographic image when irradiated with electromagnetic radiation at an exposure wavelength and that can be erased for subsequent use when irradiated with electromagnetic radiation at an erasure wavelength;
   an X-ray apparatus for exposing the storage medium at the exposure wavelength;
   a memory that stores a signal that is indicative of elapsed time since a most recent erasure of the photostimulable medium; and
   a processor for determining whether the elapsed time exceeds a limit for imaging of the medium and, when the elapsed time is determined to be above the limit but acceptable, for providing a warning to an operator of the X-ray apparatus and for enabling the operator to proceed with imaging without erasing the medium.

2. The apparatus of claim 1 further comprising a cassette for housing the medium, wherein the memory resides on the cassette and stores an analog signal.

3. The apparatus of claim 1 further comprising a cassette for housing the medium, wherein the memory resides on the cassette and stores a digital signal.

4. The apparatus of claim 1 wherein the memory resides on a host processor.

5. The apparatus of claim 1 further comprising a cassette for housing the medium and at least one indicator associated with the cassette and indicative of the elapsed time information recorded in the memory.

6. The apparatus of claim 5 wherein the indicator displays a numeric value.

7. An apparatus for obtaining a radiographic image comprising:
   an erasable photostimulable storage medium that can store a radiographic image when irradiated with electromagnetic radiation at an exposure wavelength and that can be erased for subsequent use when irradiated with electromagnetic radiation at an erasure wavelength;
   an X-ray apparatus for exposing the storage medium at the exposure wavelength;
   a memory that stores a signal that is indicative of elapsed time since a most recent erasure of the photostimulable medium; and
   a processor for determining whether the elapsed time exceeds a limit for imaging of the medium and, when the elapsed time is determined to be acceptable but above a threshold, for adjusting exposure parameters of the X-ray apparatus and proceeding with imaging without erasing the medium.

8. A method for obtaining a radiographic image using an X-ray apparatus for exposing an erasable photostimulable storage medium that can store a radiographic image when irradiated with electromagnetic radiation at an exposure wavelength and that can be erased for subsequent use when irradiated with electromagnetic radiation at an erasure wavelength, the method comprising:
   erasing the photostimulable medium;
   storing a signal that is indicative of elapsed time since the erasing of the photostimulable medium;
   determining whether the elapsed time exceeds a limit for imaging of the medium; and
   when the elapsed time is determined to be above the limit but acceptable, providing a warning to an operator of the X-ray apparatus and enabling the operator to proceed with imaging without again erasing the medium.

9. The apparatus of claim 7 further comprising a cassette for housing the medium, wherein the memory resides on the cassette and stores an analog signal.

10. The apparatus of claim 7 further comprising a cassette for housing the medium, wherein the memory resides on the cassette and stores a digital signal.

11. The apparatus of claim 7 wherein the memory resides on a host processor.

12. The apparatus of claim 7 further comprising a cassette for housing the medium and at least one indicator associated with the cassette and indicative of the elapsed time information recorded in the memory.

13. The apparatus of claim 12 wherein the indicator displays a numeric value.

14. A method for obtaining a radiographic image using an X-ray apparatus for exposing an erasable photostimulable storage medium that can store a radiographic image when irradiated with electromagnetic radiation at an exposure wavelength and that can be erased for subsequent use when irradiated with electromagnetic radiation at an erasure wavelength, the method comprising:
   erasing the photostimulable medium;
   storing a signal that is indicative of elapsed time since the erasing of the photostimulable medium;
   determining whether the elapsed time exceeds a limit for imaging of the medium; and
   when the elapsed time is determined to be acceptable but above a threshold, adjusting exposure parameters of the X-ray apparatus and proceeding with imaging without erasing the medium.

* * * * *